United States Patent [19]

Vogel et al.

[11] Patent Number: 4,698,318
[45] Date of Patent: Oct. 6, 1987

[54] PHOSPHATE GLASS CERAMIC FOR BIOLOGICAL AND MEDICAL APPLICATIONS

[75] Inventors: Jürgen Vogel; Wolfram Höland, both of Jena-Lobeda; Werner Vogel, Jena, all of German Democratic Rep.

[73] Assignee: VEB Jenaer Glaswerk, Jena, German Democratic Rep.

[21] Appl. No.: 667,038

[22] Filed: Nov. 1, 1984

[30] Foreign Application Priority Data

Jan. 24, 1984 [DD] German Democratic Rep. ...................... 2595611

[51] Int. Cl.$^4$ .......................... C03C 10/02; C03C 3/17
[52] U.S. Cl. ........................ 501/10; 501/48; 501/46; 501/47; 501/73; 128/92 VP
[58] Field of Search ...................... 501/1, 3, 10, 32, 44, 501/45, 46, 73, 48, 47; 3/1.9; 128/92 C

[56] References Cited

U.S. PATENT DOCUMENTS

| 3,519,445 | 7/1970 | MacDowell et al. | 501/47 X |
| 3,919,723 | 11/1975 | Heimke et al. | 501/153 |
| 3,981,736 | 9/1976 | Broemer et al. | 501/10 |
| 4,097,935 | 7/1978 | Jarcho | 501/1 |
| 4,120,730 | 10/1978 | Trojer et al. | 501/3 |
| 4,149,893 | 4/1979 | Aoki et al. | 501/123 |
| 4,195,366 | 4/1980 | Jarcho et al. | 501/1 |
| 4,366,253 | 12/1982 | Yagi | 501/4 |
| 4,576,920 | 3/1986 | MacDowell | 501/10 O R |

FOREIGN PATENT DOCUMENTS

| 8015044 | 1/1983 | Japan | 501/32 |
| 2087375 | 7/1982 | United Kingdom | 501/32 |

OTHER PUBLICATIONS

Peiran et al, "Preparation of Phosphate Glass Composite and their Prosthetic Application", Jour. Non-Crystaline Solids, 52 (1982) 503–510.
Zarzycki et al, "New Glass-Ceramic Materials for Prosthetic Applications, Jour. of Mat. Science, 14 (1979) 1694–1706.

Primary Examiner—William R. Dixon, Jr.
Assistant Examiner—Karl Group
Attorney, Agent, or Firm—Jordan and Hamburg

[57] ABSTRACT

A phosphate glass ceramic which can be utilized especially as biomaterial in medicine and biology. The object of the invention is to provide a glass ceramic extensively adapted to bone, possessing adjustable biologically active characteristics. Another object of the invention is to produce a glass ceramic free of $SiO_2$ or low in $SiO_2$, of high $P_2O_5$ and CaO content, possessing adjustable biologically active characteristics. The object is solved, whereby an initial glass of the composition having the mass percentages of $Al_2O_3$ 3–21, CaO 8–26, $R_2O$ 10–25, $P_2O_5$ 43–58, is provided under the condition that $R_2O$ can contain up to 25% of mass of $Na_2O$ and up to 18% of mass of $K_2O$, and is thermally treated after melting, to provide the new phosphate glass ceramic. The main crystal phases are apatite and aluminiumorthophosphate. The phosphate glass ceramic can contain additions of $SiO_2$, $B_2O_3$, $F^-$, MgO, FeO, $Fe_2O_3$, $TiO_2$.

14 Claims, No Drawings

PHOSPHATE GLASS CERAMIC FOR BIOLOGICAL AND MEDICAL APPLICATIONS

BACKGROUND OF THE INVENTION AND PRIOR ART STATEMENT

The invention refers to phosphate glass ceramic for biological applications.

The phosphate glass ceramic according to the invention can be utilized especially as biomaterial in medicine and biology, where it makes possible utilization as biomaterial in medical applications for hard tissue or bone replacement.

Because of the development of glass ceramics containing apatite, the utilization of bioactive implant materials for bone replacement has become possible in human medicine. Because the main component of human tissue is apatite, $Ca_{10}(PO_4)_6(OH,F)_2$, there results a direct intergrowth between bone tissues and the bioactive implant. Such bioactive glass ceramics containing apatite or CaO— and $P_2O_5$ based on a primary silicate glass are described in DE-OS No. 2,818,630, DE-AS No. 2,326,100 and DE-OS No. 3,306,683, as well as by Kokubo et al. (Yogyo-Kyokai-Shi No. 89,1981,45).

Although a large part of the known glass ceramics have proven in practical applications to be good to excellent, it has not yet been determined what effect long-term exposure to silicon compounds has on the human body.

A series of developments have addressed this problem; glasses high in $P_2O_5$ and CaO content, glass ceramics high in $P_2O_5$ and CaO content, and sintered ceramics high in $P_2O_5$ and CaO have been produced.

Glasses for the purpose of biological applications in the system $P_2O_5$—CaO—$Na_2O$— (MgO, BaO, $B_2O_3$) have been described by Courpied et al. (Inter. Orthopaedics 6,1982,1). The materials, however, are resorbable, do not possess any apatite crystals, and are not stable in the long term in biological media. Glasses in the system CaO—$P_2O_5$—$Al_2O_3$ are described by Wihsmann et al. (Wissenschaftliche Zeitschrift der Friedrich-Schiller-Universitaet Jena, Math.-Naturwissenschaftl. Reihe 32,2/3,1983,553). These glasses are labled as biocompatible, they contain no apatite crystals and consist of ring and chain-shaped phosphate structures of a high degree of condensation. In bone, however, there are small phosphate structural elements in the form of apatite crystals.

Although sintered ceramics rich in phosphate, as described in the U.S. Pat. No. 4,195,366, U.S. Pat. No. 4,097,935 and U.S. Pat. No. 4,149,893, possess a high crystal portion of apatite or whitlockite, they have the disadvantage that the ion exchange reactions promoting bone growth are not controllable due to the alkali contents, which are too low or are missing, as well as the minimal glass phase. Furthermore, the amorphous phase between the crystals partially is considerably washed out by reactions with bodily fluids. The same applies to the whitlockite crystals, $Ca_3(PO_4)_2$. Conventionally known $SiO_2$-free phosphate glass ceramics for biological applications, especially for bone replacements, do not contain apatite crystals. In the JP-AS No. 55-11625, the phosphate glass ceramic contains the crystal phase $\beta$-$Ca(PO_3)_2$. The glass ceramic according to the Zhu et al. (J. Non-Cryst. sol. 52,1982,503–510), which was produced in a sintering process from a glass and a crystalline compound, contains as main crystal phase $Ca_2P_2O_7$, and the foam glass ceramic according to Pernot et al. (J. Mat Sci. 14,1979,1694) contains the main crystal phase $Ca(PO_3)_2$.

According to the present state of art, therefore, an optimal union between glass ceramic and bone cannot be achieved.

SUMMARY OF THE INVENTION

The object of the invention is to provide a phosphate glass ceramic, which does not have the disadvantages of the state of art, and which is adjusted to a large degree to bone and which possesses adjustable biologically active characteristics.

Another object of the invention is to produce a phosphate glass ceramic free of $SiO_2$ or low in $SiO_2$, of high $P_2O_5$ and CaO content, extensively adapted to bone, of adjustable biologically active characteristics.

A further object is to provide a phosphate glass ceramic which can be utilized as a compact material, as a thin layer or in granulated form as a mixture, for instance, with polyurethanes as bone cement for biological applications.

An additional object is to provide a phosphate glass ceramic which has a very good biological compatability and very good biologically active characteristics, which have been proven by a union free of connecting tissues between bone and glass ceramic implant.

These and other objects and advantages of the present invention will become evident from the description which follows.

In summary, the invention relates to a phosphate glass ceramic which can be utilized especially as biomaterial in medicine and biology. The object of the invention is to provide a glass ceramic extensively adapted to bone, possessing adjustable biologically active characteristics. Another object of the invention is to produce a glass ceramic free of $SiO_2$ or low in $SiO_2$, of high $P_2O_5$ and CaO content, possessing adjustable biologically active characteristics. The object is solved, whereby an initial glass ceramic of the composition having the mass percentages of $Al_2O_3$ 3–21, CaO 8–26, $R_2O$ 10–25, $P_2O_5$ 43–58 is produced, under the condition that $R_2O$ can contain up to 25% of mass of $Na_2O$ and up to 18% of mass of $K_2O$, and is thermally treated after melting. The main crystal phases are apatite and aluminiumorthophosphate. The phosphate glass ceramic can contain additions of $SiO_2$, $B_2O_3$, F—, MgO, FeO, $Fe_2O_3$, $TiO_2$.

According to the invention, the object is solved whereby the composition of the phosphate glass ceramic consists of the following:

| | |
|---|---|
| $Al_2O_3$ | 3–21% of mass |
| CaO | 8–26% of mass |
| $R_2O$ | 10–25% of mass |
| $P_2O_5$ | 43–58% of mass |

Whereby $R_2O$ can contain up to 25% of mass of $Na_2O$ and up to 18% of mass of $K_2O$, and contains in addition to the glass phase the main crystal phase apatite or apatite and aluminiumorthophosphate. These crystal phases stimulate bone growth. In the phosphate glass ceramic according to the invention, preferably there are contained apatite fluoride, hydroxylapatite, mixed fluorine-hydroxylapatite, or by building magnesium ions and/or iron ions and/or potassium ions and/or sodium ions into the lattice of the apatite, changed apatites. This is also the case, if the glass ceramic according to the invention contains the additional components $TiO_2$, $B_2O_3$, $F^-$, $SiO_2$, FeO, $Fe_2O_3$ or MgO individually or combined in the limits of

| | |
|---|---|
| $TiO_2$ | 0–10% of mass |
| $B_2O_3$ | 0–6% of mass |
| $F^-$ | 0–7% of mass |
| $SiO_2$ | 0–7% of mass |
| FeO | 0–6% of mass |
| $Fe_2O_3$ | 0–5% of mass |
| MgO | 0–6% of mass. |

The glass ceramic material according to the invention is produced from an initial glass which is melted at 1150° C. to 1550° C. The initial glass is cooled down to below the transformation temperature or is subjected directly out of liquid molten glass to a controlled crystallization. The shaping can thereby be performed by casting as solid material or by stratification on a solid body (stratified material). If the controlled crystallization takes place only after the cooling down of the molten glass, a thermal secondary treatment of the initial glass in the temperature range of 450° C. to 650° C. is required. This process can take place in a single or several intervals in this temperature range.

Although the conventional conditions for a typical controlled crystallization, i.e. a preceding controlled phase separation, are missing, according to the composition and the thermal treatment of the molten glass of of the initial glass, a targeted precipitation of apatite or apatite and $ALPO_4$-crystals can take place. These crystal phases, which determine the characteristics of the glass ceramic, have been proven by X-ray diffraction examiniations.

A controlled crystallization in an invert glass has been accomplished for the first time with the glass ceramic according to the invention. Nuclear resonance examinations have provided quantitative proof of small phosphate structural elements, especially of orthophosphate and diphosphate groups, which have proven the invert glass character of the initial glass.

The apatite crystals give the glass ceramic according to the invention bioactive characteristics and cause it to intergrow to a high degree with bone, as has been proven in animal-experimental tests. A further essential feature in comparison to all known relevant inventions is, that in the glass ceramic according to the invention, it is possible to bring to precipitation besides apatite, simultaneously the $ALPO_4$-crystal phases, which are isotype to the quartz modifications. Under the given conditions, depending on the composition and the thermal treatment, the crystallization has to be controlled, so that in addition to apatite fluoride or hydroxylapatite, as well as besides mixed fluorine-hydroxylapatite or apatite phases, which contain iron, sodium, potassium or magnesium ions individually or in combination, aluminiumorthophosphate can be brought to precipitation. The aluminiumorthophosphate develops thereby preferably in the tridymite form and/or the berlinite form, isotype to the deep quartz. Furthermore, by building-in other ions, changed $ALPO_4$-structures can occur. Deep quartz and berlinite are piezoelectric. It has been medically proven, that electrical stimuli can enormously promote healing of bone fractures. In the present case, when mechanical stress is exerted on an implanted ceramic according to the invention, there must result piezoelectric impulses on berlinite crystals. The surface charges of the glass ceramic, which have also been proven, as well as the piezoelectric effect, lead to an optimal union between bone and bioceramic. This solution for the problem of uniting bioceramic and bone has not been described so far.

In addition to the main characteristics of the crystal phases determining the bioceramic, the phosphate glass ceramic according to the invention can contain further additional crystal phases. In some cases, these additional crystal phases, however, also have X-ray diffraction peaks, which give an indication of strongly deviating or novel, eventually also non-stoichiometric combinations.

The phosphate glass ceramic according to the invention can be utilized as a compact material, as a thin layer or in granulated form as a mixture, for instance, with polyurethanes as bone cement for biological applications.

DETAILED DESCRIPTION OF THE PREFERRED EMBODIMENTS

A survey of the compositions of the materials of the phosphate glass ceramic according to the invention is given in Table 1 in mass percentages.

Table 2 contains selected, typical examples of the consistency of the crystal phases depending on the composition and the thermal treatment of the phosphate glass ceramic according to the invention.

The crystal phases cahracterized as phosphate-mixed phases represent strongly deviating or novel, eventually also non-stoichiometric compositions.

Examinations of animal experiments have proven that the phosphate glass ceramic according to the invention has a very good biological compatibility and very good biologically active characteristics, which have been proven by a union free of connection tissues between bone and glass ceramic implant.

TABLE 1

| Example No. | $Al_2O_3$ | CaO | $P_2O_5$ | $Na_2O$ | $K_2O$ | $B_2O_3$ | $F^-$ | $SiO_2$ | MgO | FeO | $Fe_2O_3$ | $TiO_2$ |
|---|---|---|---|---|---|---|---|---|---|---|---|---|
| (Percentage of mass) | | | | | | | | | | | | |
| 1 | 20.9 | 14.0 | 49.2 | 15.9 | | | | | | | | |
| 2 | 12.8 | 15.8 | 51.9 | 17.6 | | | 1.9 | | | | | |
| 3 | 12.3 | 14.2 | 51.5 | 17.4 | | | 0.8 | | | 3.6 | 0.2 | |
| 4 | 17.2 | 13.9 | 51.6 | | 17.3 | | | | | | | |
| 5 | 14.2 | 13.1 | 48.0 | 16.1 | | 6.0 | | | | 2.6 | | |
| 6 | 14.8 | 14.3 | 50.0 | 17.4 | | | | 3.5 | | | | |
| 7 | 17.4 | 15.6 | 52.1 | 13.0 | 1.9 | | | | | | | |
| 8 | 3.2 | 24.1 | 57.3 | 15.4 | | | | | | | | |
| 9 | 12.4 | 15.9 | 52.9 | 18.0 | | | 0.8 | | | | | |
| 10 | 17.9 | 8.0 | 57.9 | 16.2 | | | | | | | | |
| 11 | 16.4 | 17.3 | 54.3 | 10.9 | 1.1 | | | | | | | |
| 12 | 16.2 | 13.1 | 48.8 | 16.2 | | | | | 5.7 | | | |
| 13 | 12.9 | 14.1 | 49.6 | 16.8 | | | 1.7 | | | 4.5 | 0.4 | |
| 14 | 16.9 | 15.1 | 43.0 | 25.0 | | | | | | | | |

TABLE 1-continued (Percentage of mass)

| Example No. | $Al_2O_3$ | CaO | $P_2O_5$ | $Na_2O$ | $K_2O$ | $B_2O_3$ | $F^-$ | $SiO_2$ | MgO | FeO | $Fe_2O_3$ | $TiO_2$ |
|---|---|---|---|---|---|---|---|---|---|---|---|---|
| 15 | 8.8 | 25.6 | 48.5 | 17.1 | | | | | | | | |
| 16 | 11.5 | 14.3 | 47.7 | 16.2 | | | 0.7 | | | | | 9.6 |
| 17 | 14.9 | 13.5 | 48.4 | 17.0 | | | | | | 1.2 | 5.0 | |
| 18 | 13.7 | 15.0 | 52.5 | 17.5 | | | 1.3 | | | | | |
| 19 | 12.1 | 13.4 | 50.1 | 16.9 | | | 0.6 | 6.9 | | | | |
| 20 | 12.9 | 13.6 | 49.8 | 16.7 | | | 7.0 | | | | | |
| 21 | 13.2 | 14.1 | 48.2 | 16.9 | | | 0.6 | | | 6.0 | 1.0 | |

TABLE 2

| Example No. | Thermal Treatment | Crystal Phases |
|---|---|---|
| 1 | 500° C., 20 h | Hydroxylapatite<br>$AlPO_4$ (tridymite form)<br>phosphate mixed phases |
| 2 | 580° C., 8 h | Apatite fluoride<br>$AlPO_4$ (berlinite form)<br>phosphate mixed phases |
| 6 | 480° C., 15 h<br>+500° C., 60 h<br>+530° C., 48 h | Hydroxylapatite<br>$AlPO_4$ (berlinite form)<br>$AlPO_4$ (tridymite form)<br>phosphate mixed phases |
| 9 | 540° C., 14 h | mixed fluorine-hydroxyl-apatite<br>$AlPO_4$ (berlinite form)<br>$AlPO_4$ (tridymite form)<br>phosphate mixed phases |
| 13 | 460° C., 48 h | Hydroxylapatite |
| 13 | 530° C., 15 h | Apatite fluoride<br>$AlPO_4$ (berlinite form)<br>phosphate mixed phases |

It thus will be seen that there is provided a phosphate glass ceramic for biological applications which attains the various objects of the invention and which is well adapted for the conditions of practical use. As numerous alternatives within the scope of the present invention, besides those alternatives, variations, enbodiments and equivalents mentioned supra, will occur to those skilled in the art, it is to be understood that the invention extends fully to all such equivalents and the like, and is to be limited only by the scope of the appended claims, and functional and structural equivalents thereof.

We claim:

1. A biologically active phosphate glass ceramic for application as hard tissue or bone replacement or implant material which comprises a phosphate glass ceramic consisting essentially of

| | |
|---|---|
| $Al_2O_3$ | 3–21% by mass, |
| CaO | 8–26% by mass, |
| $R_2O$ | [more than 10% and up to] 12–25% by mass, |
| $P_2O_5$ | 43–58% by mass, | wherein the 12–25% by mass $R_2O$ is selected from the group consisting of 12% to 25% by mass of $Na_2O$, 12% to 18% by mass of $K_2O$, and 12% to 25% $Na_2O$ and $K_2O$ together wherein the $K_2O$ content does not exceed 18% by mass and containing in addition to the glass phase the main crystal phases apatite and aluminiumorthophosphate of at least one of the tridymite form and the berlinite form, said biologically active phosphate glass ceramic having adjustable biologically active characteristics and being capable of being utilized for biological applications as a compact material, as a thin layer, or granulated form, said biologically active phosphate glass ceramic having a $SiO_2$ content no greater than 7% by mass, and having good biological compatibility with hard tissue or bone, so that said biologically active phosphate glass ceramic, when implanted, is capable of an optimal union, free of connecting tissues, between bone or hard tissue and said phosphate glass ceramic.

2. A bone cement for biological application comprising a mixture of biologically active phosphate glass ceramic of claim 1 and polyurethanes.

3. The biologically active phosphate glass ceramic of claim 1, in which the apatite comprises apatite fluoride.

4. The biologically active phosphate glass ceramic of claim 1, in which the apatite comprises hydroxylapatite.

5. The biologically active phosphate glass ceramic of claim 1, in which the apatite comprises mixed fluorine-hydroxylapatite.

6. The biologically active phosphate glass ceramic of claim 1, in which the apatite phase contains minor proportions of iron ions
and/or magnesium ions
and/or sodium ions
and/or potassium ions.

7. A bone or hard tissue implant or substitute or bone cement, comprising a biologically active phosphate glass ceramic of claim 1.

8. a biologically active phosphate glass ceramic for application as hard tissue or bone replacement or implant material which comprises a phosphate glass ceramic consisting essentially of

| | |
|---|---|
| $Al_2O_3$ | 3–21% by mass, |
| CaO | 8–26% by mass, |
| $R_2O$ | 12–25% by mass, |
| $P_2O_5$ | 43–58% by mass, |
| $TiO_2$ | 0–10% by mass, |
| $F^-$ | 0–7% by mass, |
| FeO | 0–6% by mass, |
| $Fe_2O_3$ | 0–5% by mass, |
| MgO | 0–6% by mass, | wherein the 12–25% by mass $R_2O$ is selected from the group consisting of 12% to 25% by mass of $Na_2O$, 12% to 18% by mass of $K_2O$, and 12% to 25% $Na_2O$ and $K_2O$ together wherein the $K_2O$ content does not exceed 18% by mass and containing in addition to the glass phase the main crystal phases apatite and aluminiumorthophosphate of at least one of the tridymite form and the berlinite form, said biologically active phosphate glass ceramic having adjustable biologically active characteristics and being capable of being utilized for biological applications as a compact material, as a thin layer, or in granulated form, said biologically active phosphate glass ceramic having a $SiO_2$ content no greater than 7% by mass, and having good biological compatibility with hard tissue or bone, so that said biologically active phosphate glass ceramic, when implanted, is capable of an optimal union, free of connecting tissues, between bone or hard tissue and said phosphate glass ceramic.

9. A bone or hard tissue implant or substitute or bone content, comprising a biologically active phosphate glass ceramic of claim 8.

10. A bone cement for biological applications comprising a mixture of biologically active phosphate glass ceramic of claim 8 and polyurethane.

11. The biologically active phosphate glass ceramic of claim 8, in which the apatite comprises apatite fluoride.

12. The biologically active phosphate glass ceramic of claim 8, in which the apatite comprises hydroxylapatite.

13. The biologically active phosphate glass ceramic of claim 8, in which the apatite comprises mixed fluorine hydroxylapatite.

14. The biologically active phosphate glass ceramic of claim 8, in which the apatite phase contains minor proportions of at least one of iron ions, magnesium ions, sodium ions and potassium ions.

* * * * *